April 11, 1972 A. MEILLAND Plant Pat. 3,104
ROSE PLANT
Filed Feb. 5, 1970
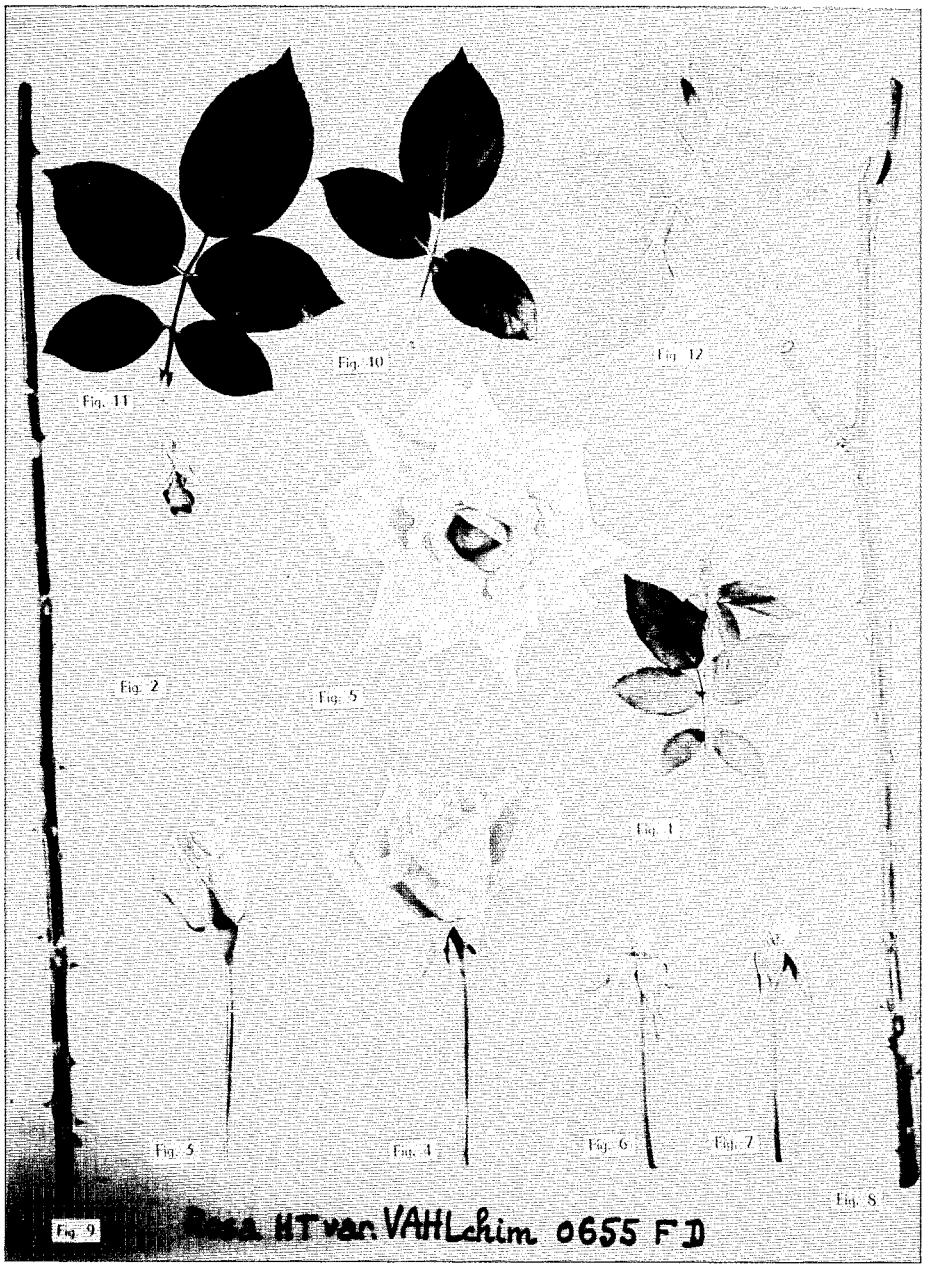
ALAIN MEILLAND
INVENTOR

United States Patent Office

Plant Pat. 3,104
Patented Apr. 11, 1972

3,104
ROSE PLANT

Alain Meilland, Alpes-Maritimes, France, assignor to The Conard-Pyle Company, West Grove, Pa.

Filed Feb. 5, 1970, Ser. No. 9,086
Claims priority, application France, Feb. 24, 1969, 6904859
Int. Cl. A01h *5/00*
U.S. Cl. Plt.—18 1 Claim

ABSTRACT OF THE DISCLOSURE

A rose plant of the hybrid tea class, discovered as a sport of the rose Carina (U.S. Plant Patent No. 2,378), but of distinct pink color and form, produced on strong growth.

SUMMARY OF THE INVENTION

The present invention is a variety of rose plant, of the hybrid tea class, whose vegetative type corresponds to that of the variety Carina (U.S. Plant Patent No. 2,378), but whose flowers are distinguishable on the inside: by a lighter and luminous pink color;
on the outside: by a light color instead of a dark pink one.

This variety, object of the present invention, is the result of a selective study made on numerous plants formed by grafting the new eye originating from the mutation of a bud of said variety Carina, and considering the interest that would no doubt be created in the horticultural industry by the disclosure of a new variety showing, as compared with the original one, an improvement of the color of its buds and, consequently, of its half-open blooms, it was advisable to propagate this new variety on a large scale in order to check its behavior, from a physical as well as a biological point of view.

The results were conclusive and underlined the importance of the disclosure of this variety with a view to its industrial exploitation by the horticulturists who produce cut flowers, as well as by the nurserymen.

The characters and properties of this new variety, obtained as indicated above, are thoroughly transmissible asexually, i.e. by any method of vegetative propagation, and in particular by grafting an eye which will be called in the trade by the name of "eye of VAHLchim 0655 F.D." and which will be found on industrial plants as well as on cut stems delivered subsequently in the trade, as has been performed by me both in the greenhouse and out of doors, at Cap d'Antibes, France, showing that the characteristics and distinctions come true to form and are transmitted through succeeding propagations.

BRIEF DESCRIPTION OF THE DRAWINGS

The accompanying drawings show typical specimens of the vegetative growth and flower of my new variety in different stages of development and as depicted in color as nearly true as it is reasonably possible to make the same in a color illustration of this character, and wherein:

FIG. 1 is a specimen of young shoot;

FIG. 2 is a specimen of a bud before the opening of the sepals;

FIG. 3 is a specimen of a bud when the sepals open;

FIG. 4 is a specimen of a flower starting to open;

FIG. 5 is a specimen of a flower, fully open, flat view;

FIG. 6 is a specimen of receptacle showing the disposition of the pistils;

FIG. 7 is a specimen of receptacle showing the disposition of the stamens;

FIG. 8 is a portion of a main cane;

FIG. 9 is a portion of a flowering stem;

FIG. 10 is a specimen of a leaf with three leaflets, upper surface;

FIG. 11 is a specimen of a leaf with five leaflets, upper surface; and

FIG. 12 is a specimen of a leaf with seven leaflets, under surface.

DETAILED DESCRIPTION OF DISCLOSURE

The following is a detailed description of my new variety in which the terminology of the color corresponds to that of the Horticultural Color Chart of the Royal Horticultural Society:

(*A*) *Plants under glass*

Class: Hybrid tea
Plant:
- Height.—1.40 m. to 1.60 m.
- Habit.—Erect

Canes:
- Color.—Young stems: Lettuce Green (H.C.C. 176–861). Mature wood: Spinach Green (H.C.C. 187–0960/2).
- Prickles.—Shape: straight; size: medium; quantity: average.
- Color: on young stems: Fern Green (H.C.C. 186–0862/3) slightly pinkish on the edges.
- On mature wood: Light hazelnut (general term).

LEAVES:
- Stipules.—adnate—more or less pectinate—with points rather short and diverging, in general.
- Petiole.—normal—edge of the vein, as well as the interior, is tinted with reddish brown; the outside is light green and shows a few hooked prickles.
- Folioles.—Number: 3–5 and 7; shape: elliptical-acuminate; teeth; normal—single; texture: leathery; size: medium; denstiy: medium; color: upper surface: Spinach Green (H.C.C. 187–0960); under surface: Lavender Green (H.C.C. 196–000761) looking at the edge, not the flat surface.

(It is to be noted that when growth starts, the foliage of the young shoots is light green and reddish brown (upper surface) and reddish, dull, on the under surface.)

*Inflorescence*:
- *Number of flowers.*—In general, one bloom to the *stem*
- *Peduncle.*—Very firm—showing a few small bristles at the base; length: from 11 to 13 centimeters; color: Lettuce Green (H.C.C. 176–861).
- *Sepals.*—Normal—the inside is slightly downy and greenish white; the outside is smooth and light green.
- *Bud.*—shape: pointed; length: 4 to 5 centimeters; color: as soon as the first petal opens, the inside is Carmine Pink (H.C.C. 75–621/2) and the outside is Rose Neyron red (H.C.C. 76–623/3) at the base and 623/1 on the outer periphery.

FLOWER: Double
- *Form.*—High-centered and sometimes somewhat globular; then, when open, projecting and overlapping petals.
- *Diameter.*—From 11 to 13 centimeters.
- *Color.*—Inside: Carmine Pink (H.C.C. 75–621/3) in the center, and 621/2 on the extreme edge of the petals. Outside: Rose Neyron Red (H.C.C. 76–623/3) then 623/2 and 623/1 on the extreme edge of the petals. (The overall tonality of the flower is pale Carmine pink on the outside, deeper and very luminous inside.)

Lasts a long time when cut.
Fragrance: The fully open flower has a light tea odor.

Corolla:

*Petals.*—Texture: very firm; the base of the first petals is wide and rounded; it is narrower for the central petals—the unguis is yellowish—the first outside petal sometimes shows a median vein, more or less pronounced, of greenish color, which gives it a rather strongly blistered aspect. Number: 35 on average.

*Stamens.*—Number: 170 average; anthers: normal—yellow, slight reddish; filaments: of average length—the longest ones are greenish white, slightly pink; the short ones are pinkish; pistils: number: 100 on an average; stigmas: normal, yellowish; styles: rather strangled and twisted when coming out of the receptacle; slightly hairy and surrounded with a thick collar of silky hairs—greenish yellow at base, tip light Fuchsine Red.

Development:

*Vegetation.*—Quite vigorous

*Aptitude for repeat-blooming.*—Very good.

*Resistance to diseases.*—Excellent.

(*B*) *Plants in the open air*

The following points of differences were noted in the open air plant, as compared with a plant under glass such as has been described above:

Plant:

*Height.*—Om. 80.

*Habit.*—Erect, somewhat open.

Canes:

*Color.*—The young stems usually take on a reddish brown color on the side exposed to the sun.

*Prickles.*—Color: first of all reddish, then pinkish green and lastly light hazelnut (general terms)

(They are sometimes intermingled with britles on the suckers.)

Foliage:

*Folioles.*—Generally smaller than those observed under glass—their texture is more leathery and less dull.

*Color.*—Inside: Spinach Green (H.C.C. 187, a little darker than 0960); outside: Lavender Green (H.C.C. 196, a little cruder Green than 000761)

Inflorescence:

*Peduncle.*—Length: 9 to 10 centimeters; color: light Green, more or less spotted with reddish brown.

*Sepals.*—The greenish white of the inside is sometimes spotted with Fuchsine red. The outside is light Green and reddish brown.

*Bud.*—Shape: conical. Color: inside: Carmine Pink (H.C.C. 75–621/2 and 621/1 in depth. Outside: Rose Neyron Red (H.C.C. 76–623/2 at base and 623/1 on the outer periphery, with more or less pronounced spots of 623).

*Flower.*—When full-blown, a light suffusion of Rose Neyron Red (H.C.C. 76–623/1 and 623) appears on the folded edge of the petals, and especially on the outer periphery. Duration: lasts a long time, either on the plant, or when cut.

*Corolla.*—Petals: 40 to 45.

*Receptacle.*—Normal—smooth—light green—sometimes, above the crown, some protuberances spread out—more or less swollen; they are hairy inside, smooth on the outside, and carry some stamens.

Development:

*Resistance to Spring frost.*—Normal.

*Resistance to Winter frost.*—Strong.

*Resistance to diseases.*—Especially good.

I claim:

1. A new and distinct variety of rose plant of the hybrid tea class, substantially as herein shown and described, characterized by the novelty of the plant, from the physical point of view, in that the plant has Spinach Green mature wood, is erect, the flower is double, light Carmine Pink, its petals are very film and give it a high-centered form at first, sometimes a little globular, then when open, the petals are protruding and overlapping; and from the biological point of view, the plant has a very strong vegetation, either under glass or in the open air, a great capacity for repeat-blooming, excellent resistance to fungus diseases, its flowers last a long time, either on the plant or when cut, and the petals drop off cleanly.

No references cited.

R. E. BAGWILL, Primary Examiner